(12) United States Patent
Watts et al.

(10) Patent No.: US 9,212,148 B2
(45) Date of Patent: Dec. 15, 2015

(54) FUNCTIONALIZING REAGENTS AND THEIR USES

(71) Applicant: Glythera Limited, Newcastle Upon Tyne (GB)

(72) Inventors: Andrew Graham Watts, Bath (GB); Terrence Kantner, Bath (GB); Amanda Barbara MacKenzie, Bath (GB)

(73) Assignee: Glythera Limited, Newcastle Upon Tyne (GB)

( * ) Notice: Subject to any disclaimer, the term of this patent is extended or adjusted under 35 U.S.C. 154(b) by 0 days.

(21) Appl. No.: 14/315,784

(22) Filed: Jun. 26, 2014

(65) Prior Publication Data

US 2014/0364586 A1 Dec. 11, 2014

Related U.S. Application Data

(62) Division of application No. 13/140,690, filed as application No. PCT/GB2009/002924 on Dec. 21, 2009, now Pat. No. 8,785,595.

(60) Provisional application No. 61/139,014, filed on Dec. 19, 2008.

(30) Foreign Application Priority Data

Dec. 19, 2008 (GB) .................................. 0823309.0

(51) Int. Cl.
| | | |
|---|---|---|
| *C07D 213/55* | (2006.01) | |
| *C07D 213/38* | (2006.01) | |
| *C07D 213/80* | (2006.01) | |
| *C07D 239/28* | (2006.01) | |
| *A61K 47/48* | (2006.01) | |
| *C07D 213/30* | (2006.01) | |
| *C07D 213/46* | (2006.01) | |
| *C07H 15/26* | (2006.01) | |
| *C07K 5/08* | (2006.01) | |
| *C07K 1/13* | (2006.01) | |

(52) U.S. Cl.
CPC ........ *C07D 239/28* (2013.01); *A61K 47/48215* (2013.01); *C07D 213/30* (2013.01); *C07D 213/38* (2013.01); *C07D 213/46* (2013.01); *C07D 213/55* (2013.01); *C07D 213/80* (2013.01); *C07H 15/26* (2013.01); *C07K 5/08* (2013.01); *C07K 1/13* (2013.01)

(58) Field of Classification Search
CPC . A61K 213/55; A61K 213/38; A61K 213/46; A61K 213/80; C07D 239/28
See application file for complete search history.

(56) References Cited

U.S. PATENT DOCUMENTS

| | | | | |
|---|---|---|---|---|
| 5,900,461 | A | * | 5/1999 | Harris ........................ 525/54.11 |
| 2001/0044526 | A1 | * | 11/2001 | Shen ............................ 530/409 |
| 2004/0116649 | A1 | | 6/2004 | Kozlowski |
| 2012/0101254 | A1 | | 4/2012 | Watts et al. |

FOREIGN PATENT DOCUMENTS

| | | |
|---|---|---|
| WO | 8805433 A1 | 7/1988 |
| WO | 9216221 A1 | 10/1992 |
| WO | 9741897 | 11/1997 |
| WO | 03061577 A2 | 7/2003 |

OTHER PUBLICATIONS

Inokuma, S. et al., "Synthesis and Complexing Properties of [2,n](2,6)Pyridinocrownophanes", J. Org. Chem., 70: 1698-1703 (2005).
Inokuma, S. et al., "Synthesis of crownophanes possessing bipyridine moieties: bipyridinocrownophanes exhibiting perfect extractability toward AG + ion", Tetrahedron, 62: 10005-10010 (2006).
Inokuma, S. et al., "Synthesis of crownophanes possessing three pyridine rings", Tetrahedron, 63: 5088-5094 (2007).
Benmansour, K. et al., "Ionic conductivity of poly[N-(3,6,9-trioxadecyl)-4-vinylpyridinium)] salts with univalent counter-ions in aqueous solutions", European Polymer Journal, 3(; 1443-1449 (2003).
Gauthier, M. et al., "Peptide/protein-polymer conjugates: synthetic strategies and design concepts", Chem. Commun., 2591-2611 (2008).
Roberts, M.J. et al., "Chemistry for peptide and protein PEGylation", Advanced Drug Delivery Reviews, 54: 459-476 (2002).
Morpurgo, M. et al., "Preparation and Characterization of Poly(ethylene glycol) Vinyl Sulfone", Bioconjugate Chem., 7: 363-368 (1996).
Crankshaw, M.W. et al., "Modification of Cysteine", Current Protocols in Protein Science, Unit 15.1, pp. 1-18 (1996).

* cited by examiner

*Primary Examiner* — Michael G Hartley
*Assistant Examiner* — Jagadishwar Samala
(74) *Attorney, Agent, or Firm* — Patrick J. Hagan; Dann, Dorfman, Herrell and Skillman, P.C.

(57) ABSTRACT

Reagents and methods for functionalizing polypeptides with moieties (alkylene glycol) molecules and glycan groups are disclosed that are based on a functionalizing reagent which comprises a nitrogen containing heterocyclic aromatic ring having a vinyl substituent that is capable of reacting with one or more thiol groups that are naturally present, or have been introduced into, the polypeptide, for example by employing a thiol group of one or more cysteine residues. The functionalizing reagent is covalently linked to a poly(alkylene glycol) molecule, such as a polyethylene glycol (PEG) molecule, or a glycan group so that the reaction between the vinyl group and the thiol group in the polypeptide covalently links the polypeptide to the poly(alkylene glycol) molecule and/or the glycan group.

11 Claims, 4 Drawing Sheets

FUNCTIONALIZING REAGENTS AND THEIR USES

CROSS-REFERENCE TO RELATED APPLICATIONS

This application is the divisional of U.S. patent application Ser. No. 13/140,690, filed Dec. 5, 2011, which is the U.S. National Stage of International Application No. PCT/GB2009/002924, filed Dec. 21, 2009, which claims benefit of U.S. Provisional Application No. 61/139,014, filed Dec. 19, 2008 and GB Application No. 0823309.0, filed Dec. 19, 2008. The entire disclosure of each of the aforesaid applications is incorporated by reference in the present application.

FIELD OF THE INVENTION

The present invention relates to functionalising reagents and methods of using them for the modification of proteins and polypeptides. The present invention further relates the uses of functionalised polypeptides produced by the methods of the present invention. More specifically, the present invention employs functionalising reagents comprising a nitrogen containing heterocyclic aromatic ring which has a vinyl substituent and which is covalently linked to a coupling partner. Typically, the coupling partner is capable of altering properties of the polypeptide such as a poly(alkylene glycol) molecule or a glycan group.

BACKGROUND OF THE INVENTION

It is known in the art that it is possible to covalently link polyethylene glycol (PEG) polymers to therapeutic polypeptides, a process termed pegylation. Pegylation is normally carried out reacting the polypeptide with a reactive derivative of the PEG molecule, typically using a derivative that includes a functional group such as a hydroxyl, a thiol, an amine or a carboxylic acid group. In pegylation reactions, the reactive functional group of the PEG molecule forms a stable covalent bonds with amino, carboxy or thiol groups of amino acids present in the polypeptide, or with the reactive N- or C-termini of the polypeptide. In general, pegylation reactions require the use of a reactive cross-linking reagent such as maleimide.

However, it is also known that pegylation is a relatively uncontrolled reaction, mainly as a result of the use of the reactive cross-linker and because the PEG molecules can react in a number of different ways with multiple functional groups present in polypeptides, thereby producing heterogeneous products. This means that the resulting pegylated polypeptides can have linear or branched structures and/or have a variable number of PEG molecules coupled to each polypeptide. The reaction is also influenced by factors such as protein type and concentration, reaction time, temperature and pH value, all of which have an effect on the end products of the reaction.

In general, pegylation is carried out to influence the pharmacokinetic or immunological properties of polypeptides, especially those that are intravenously administered. In particular, the polypeptides can be altered to improve their stability, biological half-life, water solubility and immunologic characteristics. It is thought that pegylating a polypeptide to increase its mass (e.g., by 20-50 kDa) means that it is less readily excreted through the kidneys and therefore persists in the body for longer. In addition, pegylated polypeptides are thought to be protected from the degradation by endogenous enzymes, which also helps to increase their in vivo half-life.

It is further thought that increasing the in vivo half-life and improving the efficacy of polypeptide drugs can lead to a reduction in the frequency or dose of the polypeptide that a patient requires, and hence help to reduce immune reactions against the polypeptide. Pegylation can also help to improve the water solubility to hydrophobic polypeptides.

However, while the properties of pegylated polypeptides are desirable, especially in therapeutic polypeptides, the lack of control in the pegylation reactions remains a problem as it often leads to a range of products having a range of different properties. Moreover, as polypeptides are complex molecules, it is difficult to use protecting groups to control the site and/or extent of the reaction, for example as would be possible in small molecule chemistry.

The glycosylation of polypeptides is a natural form of post-translational modification that alters the structure and function of polypeptides. In nature, glycosylation is introduced by an enzymatic process that leads to site specific modification of different types of glycosylated polypeptides. In N-linked glycosylation, glycans are attached to the amide nitrogen of asparagine side chains and in O-linked glycosylation, glycans are attached to the hydroxy oxygen of serine and threonine side chains. Other forms of glycosylation include glycosaminoglycans which are attached to the hydroxy oxygen of serine, glycolipids in which the glycans are attached to ceramide, hyaluronan which is unattached to either protein or lipid, and GPI anchors which link proteins to lipids through glycan linkages.

There is a general problem in the art in that glycosylation is often added to polypeptides in eukaryotic cells, but is rarely added to polypeptides expressed in the prokaryotic hosts often used for the recombinant expression of therapeutic polypeptides. This absence of glycosylation in polypeptides produced in prokaryotic hosts can lead to the polypeptides being recognised as foreign or mean that they have the properties that otherwise differ from their native forms. There is also a problem that it is difficult to engineer glycosylation into polypeptides at sites where there is not native glycosylation, in an attempt to use this to modulate the properties of the polypeptides.

WO 88/05433 discloses cross-linking reagents for producing conjugates of polypeptides and signal producing or cytotoxic chemical entities. The cross-linking reagents consist of a range of aromatic nitrogen-containing heterocyclic compounds, in particular 2-, 3- or 4-vinyl pyridines and vinyl pyrimidines, to which the signal producing or cytotoxic chemical entities can be attached via activated ester substituents present in the cross-linking reagent. The conjugation reaction relies on the vinyl groups of the reagents reacting with thiol groups present in the polypeptides. The compounds disclosed in WO 88/05433 all include an electron withdrawing substituent as a functional group of the aromatic nitrogen-containing heterocyclic ring. It is also notable that WO 88/05433 does not provide any examples that show the linkage of the signal producing or cytotoxic chemical entities to a polypeptide using the cross-linking reagents.

WO 2005/024041 describes a method of mass-tagging proteins in two or more cell populations for use in proteomics methods. The tagging involves reacting cysteine residues in one of the populations with 2-vinylpyridine, and in the other population with a $C_{1-4}$ alkyl substituted 2-vinylpyridine, thereby producing tagged proteins with masses that are distinguishable by mass spectroscopy.

Banas et al (Biochimica et Biophysica Acta, 957(2): 178-84, 1988) studied the reactivity of cysteine residues of *E. coli* phosphofructo-1-kinase, using vinyl pyridine, bromopyruvate and dithionitrobenzoic acid to determine the relative reactivity of the six cysteine residues present in the polypeptide.

Fullmer (Analytical Biochemistry, 142(2): 336-9, 1984) describes a method of improving the analysis of the amino acid composition of peptides, in particular the identification of cysteine and tryptophan. One of the improvements uses 4-vinyl pyridine to protect half of the cysteine residues present in a peptide after reductive cleavage of disulphide bonds as the cysteine derivatives produced are stable to acid hydrolysis.

There remains a problem in the art in improving the derivatisation of polypeptides with coupling partners such as PEG molecules and glycan groups.

SUMMARY OF THE INVENTION

Broadly, the present invention relates to compounds and methods of using them for functionalising polypeptides with moieties, such as poly(alkylene glycol) molecules and glycan groups. This chemistry is based on a functionalising reagent which comprises a nitrogen containing heterocyclic aromatic ring having a vinyl substituent that is capable of reacting with one or more thiol groups that are naturally present, or have been introduced into, the polypeptide, for example by employing a thiol group of one or more cysteine residues. In general, the functionalising reagent is covalently linked to a poly(alkylene glycol) molecule, such as a polyethylene glycol (PEG) molecule, or a glycan group so that the reaction between the vinyl group and the thiol group in the polypeptide covalently links the polypeptide to the poly(alkylene glycol) molecule and/or the glycan group.

Accordingly, in one aspect, the present invention provides a method which comprises contacting a polypeptide having at least one reactive thiol group with a functionalising reagent which comprises a nitrogen containing heterocyclic aromatic ring having a vinyl substituent capable of reacting with the at least one thiol group of the polypeptide, wherein the functionalising reagent is covalently linked to a poly(alkylene glycol) molecule and/or a glycan group, so that the vinyl substituent of the functionalising reagent reacts with the thiol group of the polypeptide, thereby to covalently link the poly(alkylene glycol) molecule or glycan group to the polypeptide.

In a further aspect, the present invention provides a method of modifying, e.g. pegylating or glycosylating, a polypeptide having at least one reactive thiol group, the method comprising contacting the polypeptide with a functionalising reagent which comprises a nitrogen containing heterocyclic aromatic ring having a vinyl substituent capable of reacting with the at least one thiol group of the polypeptide, wherein the functionalising reagent is covalently linked to a poly(alkylene glycol) molecule, e.g. polyethylene glycol (PEG) molecule, or a glycan group, so that the vinyl substituent of the functionalising reagent reacts with the thiol group of the polypeptide, thereby to covalently link the poly(alkylene glycol) molecule or glycan group to the polypeptide.

The methods of the present invention may involve one or more steps in addition to the step of reacting the functionalising reagent and the polypeptide to link them together. By way of example, the methods may include an initial step of reacting a precursor functionalising reagent comprising a nitrogen containing heterocyclic aromatic ring having a vinyl substituent with the poly(alkylene glycol) molecule or glycan group to produce the functionalising reagent. Alternatively or additionally, the method may comprise the initial steps of determining the location of reactive thiol groups in the polypeptide, selecting one or more thiol groups for reaction with a functionalising reagent according to the present invention, and optionally protecting some of the remaining thiol groups. The polypeptide may then be reacted with the functionalising reagent as described herein. It will be appreciated from the above that the reaction of the vinyl group and a thiol group of the polypeptide generally produced a —$CH_2$—$CH_2$—S— group, covalently linking the functionalising reagent and the polypeptide. The thioether bond produced in this reaction is generally very stable under biological conditions. This stability may be contrasted with the prior art use of maleimide as a cross-linking reagent which suffers from the potential disadvantage when used to derivatise a polypeptide that it undergoes reactions such as ring opening on storage.

In embodiments of the present invention in which the polypeptide does not include a suitable thiol group, or does not include suitable thiol group in a desired position in the polypeptide chain, the present invention may comprises the initial step of modifying a parent polypeptide, e.g. by chemical reaction or site directed mutagenesis, to produce a variant polypeptide having a thiol group at one or more desired positions of the polypeptide. Preferably, this is done by replacing one or more of the amino acids in the polypeptide with a cysteine residue. In embodiments of the present invention relating to the glycosylation of polypeptides, the parent polypeptide may be modified at a natural glycosylation site, for example at an aspargine, a threonine or a serine residue, to introduce a thiol group that can then react with a functionalising reagent that comprises one or more glycan groups. This may be done, for example, where the parent polypeptide is not glycosylated at this position, for example as a result of the way in which it has been produced, or where glycosylation has been removed.

Alternatively or additionally, the methods of the present invention may involve modifying amino acid residues spatially proximal to the reactive thiol group to improve the reactivity of the thiol group towards the functionalising reagent. By way of example, modifications to spatially proximal amino acid residues may be performed to alter local pH, hydrogen bonding interactions, waters of hydration, or steric accessibility around the reactive thiol group.

Preferably, the reactive thiol group, whether it is present naturally in the polypeptide or has been introduced, is part of a cysteine amino acid residue.

After the method as defined above has been carried out, the pegylated or glycosylated polypeptide may then be purified or isolated in one or more further steps.

In a further aspect, the present invention provides a compound for functionalising a polypeptide with a poly(alkylene glycol) or glycan group represented by the formula:

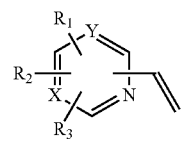

wherein:

X and Y are independently selected from CH or N;

wherein at least $R_1$, and optionally $R_2$, are covalently linked to a poly(alkylene glycol) molecule and/or a glycan group;

wherein:

$R_1$, and optionally $R_2$, are independently selected from:

—$(CH_2)_n$—Z—$(CH_2)_o$—R, where Z is O, S or NH, n is 0 to 10, o is 0 to 10 and where R is a hydrogen, a poly(alkylene glycol) molecule or a glycan group; or —C(O)—Z—$(CH_2)_o$—R, Z is O, S or NH, o is 0 to 10 and where R is a hydrogen, a poly(alkylene glycol) molecule or a glycan group; or —$(CH_2)_n$—Z—C(O)—$(CH_2)_o$—R, where Z is O, S or NH, n is 0 to 10, o is 0 to 10 and where R is a hydrogen, a poly(alkylene glycol) molecule or a glycan group; or —Y—$(CH_2)_n$—Z—C(O)—$(CH_2)_o$—R, where Y is an aryl group, O, S or NH, Z is O or NH, n is 0 to 10, o is 0 to 10 and where R is a hydrogen, a poly(alkylene glycol) molecule or a glycan group; or —Y—R, where Y is O or S, R is a hydrogen, a glycan, a poly(alkylene glycol) molecule, aryl or $C_{1-10}$ alkyl;

with the proviso that when $R_2$ is not linked to a poly(alkylene glycol) molecule or a glycan group, it may additionally be selected from hydrogen or an electron withdrawing group, such as halogen (F, Cl, or Br), —$NO_2$, —$CO_2H$, —$CO_2R_4$, $COR_4$, —CHO, —CN, —$CF_3$, —$SO_2NR_4R_5$, alkyl or phenyl, where $R_4$ and $R_5$ are independently selected from hydrogen or $C_{1-10}$ alkyl;

or $R_2$ and $R_3$ together form a fused (hetero)aromatic ring substituent which may include, but is not limited to, an indole, indazole, benzimidazole, quinoline, isoquinoline, aziradine or a purine;

or $R_3$ is selected from hydrogen or a substituent selected from halo; hydroxy; ether (e.g., $C_{1-7}$alkoxy); formyl; acyl (e.g., $C_{1-7}$alkylacyl, $C_{5-20}$arylacyl); carboxy; ester; acyloxy; amido; acylamido; thioamido; tetrazolyl; amino; nitro; nitroso; azido; cyano; isocyano; cyanato; isocyanato; thiocyano; isothiocyano; thioether (e.g., $C_{1-7}$alkylthio); sulfonic acid; sulfonate; sulfone; sulfonyloxy; sulfinyloxy; sulfamino; sulfonamino; sulfinamino; sulfamyl; sulfonamido; $C_{1-7}$alkyl (including, e.g., unsubstituted $C_{1-7}$alkyl, $C_{1-7}$haloalkyl or $C_{1-7}$hydroxyalkyl, $C_{1-7}$-carboxyalkyl, $C_{1-7}$-aminoalkyl).

In some embodiments, for the linkers described above, Y is O or NH, with the other groups as defined above. Additionally or alternatively, the electron withdrawing group is not an alkyl group.

Preferably, the nitrogen containing heterocyclic aromatic ring is a substituted pyridine ring (X and Y are both CH) or a substituted pyrimidine ring (one of X and Y is CH and the other is N).

Preferably, the $R_1$ and/or $R_2$ groups for linking the poly(alkylene glycol) molecule and/or the glycan group to the nitrogen containing heterocyclic aromatic ring are independently selected from —$(CH_2)_n$—Z—$(CH_2)_o$—R or —C(O)—Z—$(CH_2)_o$—R, with the substituents as defined above. More preferably, in the $R_1$ and $R_2$ groups, o is zero and the groups may be represented as —$(CH_2)_n$—Z—R or —C(O)—Z—R, with the substituents as defined above.

By including the possibility that one or two of the groups linked to the nitrogen containing heterocyclic aromatic ring may be poly(alkylene glycol) molecule and/or glycan groups, the present invention enables $R_1$ and $R_2$ to both be poly(alkylene glycol) molecules or glycan groups or one to be a poly(alkylene glycol) molecule and one a glycan group, thereby producing mixed functionalising reagents.

Preferably, the nitrogen containing heterocyclic aromatic ring is a pyridine, pyrimidine or azidine ring. More preferably, the nitrogen containing heterocyclic aromatic ring is a pyridine ring or a pyrimidine ring and most preferably, it is a pyridine ring. When pyridine or pyridimidine rings are employed, preferably the vinyl group is in the 2-position relative to a nitrogen heteroatom.

However, in some embodiments, it is possible to employ more extended fused heterocyclic aromatic ring systems such as an indole, indazole, benzimidazole, quinoline, isoquinoline, aziradine or a purine.

Generally, the poly(alkylene glycol) molecule or glycan group is directly covalently bonded to the $R_1$ and/or $R_2$ groups as shown in the formula above. The linking groups may have different lengths to keep the poly(alkylene glycol) molecule or the glycan group closer or further away from the polypeptide. The length of the linker may be chosen However, in some embodiments it might be desirable to include an extended linker between the $R_1$ group and the poly(alkylene glycol) molecule or glycan group. Such a linker may be necessary to alter solubility or immunogenic properties of the functionalising group.

A preferred class of functionalising reagents according to the present invention may be represented by the following general formula:

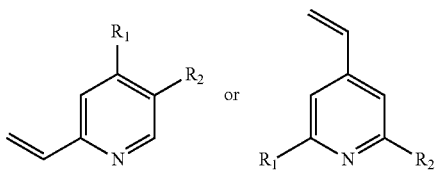

wherein:
at least $R_1$, and optionally $R_2$, are covalently linked to a poly(alkylene glycol) molecule and/or a glycan group;
and further wherein:
$R_1$, and optionally $R_2$, are independently selected from:

—$(CH_2)_n$—Z—$(CH_2)_o$—C(O)—R, where Z is O, S or NH, n is 0 to 10, o is 0 to 10 and where R is a hydrogen, a poly(alkylene glycol) molecule or a glycan group; or —$(CH_2)_n$—Z—$(CH_2)_o$—R, where Z is O, S or NH, n is 0 to 10, o is 0 to 10 and where R is a hydrogen, a poly(alkylene glycol) molecule or a glycan group; or —C(O)—Z—$(CH_2)_o$—R, Z is O, S or NH, o is 0 to 10 and where R is a hydrogen, a poly(alkylene glycol) molecule or a glycan group; or —$(CH_2)_n$—Z—C(O)—$(CH_2)_o$—R, where Z is O, S or NH, n is 0 to 10, o is 0 to 10 and where R is a hydrogen, a poly(alkylene glycol) molecule or a glycan group; or —Y—$(CH_2)_n$—Z—C(O)—$(CH_2)_o$—R, where Y is an aryl group, O, S or NH, Z is O or NH, n is 0 to 10, o is 0 to 10 and where R is a hydrogen, a poly(alkylene glycol) molecule or a glycan group; or —Y—R, where Y is O or S, R is a hydrogen, a glycan, a poly(alkylene glycol) molecule, aryl or $C_{1-10}$ alkyl;

with the proviso that when $R_2$ is not linked to a poly(alkylene glycol) molecule or a glycan group, it may additionally be selected from hydrogen or an electron withdrawing group, such as halogen (F, Cl, or Br), —$NO_2$, —$CO_2H$, —$CO_2R_4$, $COR_4$, —CHO, —CN, —$CF_3$, —$SO_2NR_4R_5$, alkyl or phenyl, where $R_4$ and $R_5$ are independently selected from hydrogen or $C_{1-10}$ alkyl.

In a preferred class of functionalising reagents, $R_1$ is —$(CH_2)_n$—Z—$(CH_2)_o$—C(O)—R, where Z is O, S or NH, n is 0 to 10, o is 0 to 10 and where R is one or more poly(alkylene glycol) molecules or glycan groups; and/or $R_2$ is a hydrogen, alkyl or —$(CH_2)_n$—Z—$(CH_2)_o$—C(O)—R, where Z is O, S or NH, n is 0 to 10, o is 0 to 10 and where R is one or more poly(alkylene glycol) molecules or glycan groups.

In a further aspect, the present invention provides a polypeptide conjugate comprising one or more poly(alkylene glycol) molecules or glycan groups, wherein the polypeptide a therapeutic polypeptide which is covalently linked to the poly(alkylene glycol) molecule or glycan group via a thiol group present in the polypeptide and a functionalising reagent as defined above.

In a further aspect, the present invention provides a polypeptide conjugate as defined above for use in therapy.

Embodiments of the present invention will now be described by way of example and not limitation with reference to the accompanying figures.

BRIEF DESCRIPTION OF THE FIGURES

FIG. 5A: structure of PL-LK-07; FIG. 5B: liquid chromatograph of product of protein functionalization reaction; and FIG. 5C: SDS PAGE analysis of model protein functionalized with PEG molecules.

DETAILED DESCRIPTION

Polypeptides

Figure 1:
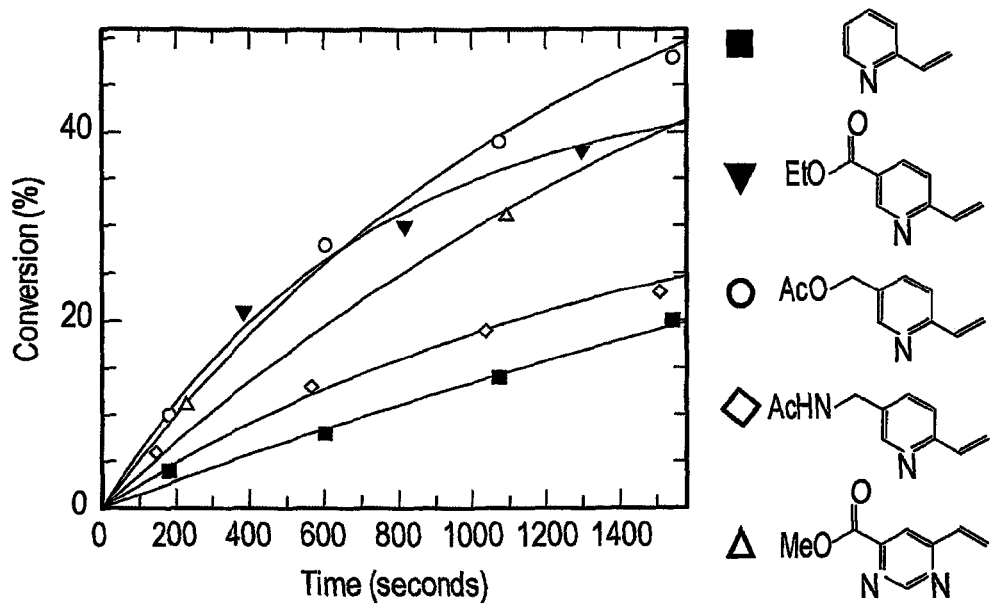
FIG. 1. Relative rates of reaction of a range of linkers with glutathione.

The methods of the present invention are generally applicable to a range of applications based on the reaction being capable of specifically and directly introducing functional groups, in particular poly(alkylene glycol) molecules and glycan groups, into polypeptides. The methods described are applicable to any size or type of polypeptide from single amino acids and peptides to polypeptides and proteins having molecular weights of up to or over 100 kDa. Accordingly, while for convenience, the methods herein are generally described by reference to "polypeptides", this should be taken to include shorter sequences of amino acids (e.g., from 2, 3, 4, 5 or 10 amino acids in length to 30, 40 or 50 amino acids in length), sometimes referred to in the art as peptides. The term should also be taken to include polypeptides having secondary, tertiary or quaternary structure generally referred to as proteins, as well as multidomain proteins.

The methods and reagents disclosed herein are particularly useful for functionalising therapeutic polypeptides, for example to modify their pharmacological properties such as stability, biological half-life or water solubility, or the immunologic characteristics of the polypeptide.

Example of suitable classes of polypeptides that may be modified in accordance with the present invention include erythropoietins (EPO), interferons, interleukins, chemokines, lymphokines, cytokines, insulin, monoclonal antibodies and fragments, recombinant antibodies and fragments, blood-clotting factors, colony-stimulating factors (CSFs), growth hormones, plasminogen activators, virally-derived peptides, reproductive hormones, therapeutic enzymes and carrier proteins (e.g. as used to make conjugate vaccines). Specific examples of polypeptides that may be employed include colony stimulating factor (CSF), granulocyte colony stimulating factor (G-CSF), granulocyte macrophage colony stimulating factor (GM-CSF), Factor VIIa, Factor VIII, Factor IX, human growth hormone (hGH), DNase, insulin, glucagon, VEGF, VEGF receptor, TNF, TNF receptor, platelet-derived growth factor (PDGF), tissue plasminogen activator (tPA), erythropoietin (EPO), enfurvirtide, insulin-like growth factor (IGF), nerve growth factor (NGF), IL-1, IL-2, IL-6, IL-10, IL-12, IL-18, IL-24, interferon beta-1a, interferon beta-1b, interferon alpha-2a, interferon alpha-2b, interferon alpha, or interferon gamma.

In the present invention, references to polypeptides that are antibodies includes immunoglobulins whether natural or partly or wholly synthetically produced. The term also covers any polypeptide or protein comprising an antigen binding domain. Antibody fragments which comprise an antigen binding domains include Fab, scFv, Fv, dAb, Fd fragments, diabodies, triabodies or nanobodies. It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP 0 184 187 A, GB 2,188,638 A or EP 0 239 400 A. Antibodies can be modified in a number of ways and the term should be construed as covering any specific binding member or substance having an antibody antigen-binding domain with the required specificity. Thus, this term covers antibody fragments and derivatives, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP 0 120 694 A and EP 0 125 023A.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242; 423-426, 1988; Huston et al, PNAS USA, 85: 5879-5883, 1988); (viii) bispecific single chain Fv dimers (PCT/US92/09965) and (ix) "diabodies", multivalent or multispecific fragments constructed by gene fusion (WO 94/13804; Holliger et al, P.N.A.S. USA, 90: 6444-6448, 1993). Fv, scFv or diabody molecules may be stabilised by the incorporation of disulphide bridges linking the VH and VL domains (Reiter et al, Nature Biotech, 14: 1239-1245, 1996). Minibodies comprising a scFv joined to a CH3 domain may also be made (Hu et al, Cancer Res., 56: 3055-3061, 1996).

Methods of Modifying or Functionalising Proteins

The present invention provides a convenient method for modifying or functionalising a protein of interest using thiol groups that are present in, or have been previously introduced into, the polypeptide, e.g. at one or more cysteine residues. In preferred embodiments, the methods disclosed herein employ reagents and conditions that are well adapted for modifying proteins and other biological materials. In particular, the reaction conditions that are used in the present method helps to avoid the problems that tend to occur when using prior art reagents such as maleimide, which have a tendency to produce a mixture of different products with a range of different properties. As mentioned above, the polypeptide of interest may be modified using existing thiol groups or by introducing thiol groups in an initial step of the method, for example by reacting one or more functional groups of the polypeptide to produce a thiol group, or by introducing a thiol group or a precursor thereof into the polypeptide. By way of example, this may involve the step of introducing a cysteine residue into the polypeptide at a site where it is desired to functionalise the polypeptide. This may be useful in situations where a convenient cysteine residue for reaction according to the present invention is not present in a starting or wild-type polypeptide. Conveniently, this may be achieved using site directed mutagenesis of the polypeptide, the use of which is well established in the art.

The present methods are particularly amenable for use in functionalising polypeptides with poly(alkylene glycol) molecules or glycan groups. One preferred use of the methods and reagents of the present invention is for glycosylating a polypeptide of interest with one or more glycan groups. The carbohydrate group may be a naturally occurring or synthetic monosaccharide, oligosaccharide or polysaccharide. This approach can be used to add glycosylation to a protein of interest, or to introduce glycosylation where glycosylation is desired but is not introduced in the course of the production of the protein, e.g. by virtue of the fact that the protein has been produced in bacterial cells or, particularly for peptides, where they have been produced by chemical synthesis.

The ability to control glycosylation at defined sites using the present invention represents a useful tool for engineering recombinant proteins, for example therapeutic proteins and antibodies, and fragments thereof, in their manufacture and in controlling their immunogenicity and pharmacological properties such as half life. At present, the manufacture of recombinant protein therapeutics is expensive and slow as mammalian cell lines are often used for manufacture to ensure that the proteins are glycosylated. The methods disclosed herein may be used to add glycosylation to a polypeptide after production in bacterial cell lines, in which expression is generally more efficient, thereby helping to improve the speed and/or economy of protein production, while retaining the glycosylation. Alternatively, for polypeptides expressed in cell lines that glycosylate expression products, the present invention may be used to modify or add glycosylation.

In preferred embodiments, the carbohydrates employed may comprise chemically modified derivatives of naturally occurring branched oligosaccharides commonly displayed on N- or O-linked glycoproteins, or degradation products thereof. Carbohydrate groups that may be used in the present invention are well known in the art and include carbohydrate groups found in the N- and O-linked glycosylation of eukaryotic proteins and man made carbohydrate groups, e.g. see the carbohydrate groups and methods of producing and identifying them disclosed in WO 03/025133 and WO2004/083807.

N-Linked glycans are found attached to the R-group nitrogen (N) of asparagine in the sequon. The sequon is a Asn-X-Ser or Asn-X-Thr sequence, where X is any amino acid except proline and may be composed of N-acetyl galactosamine, galactose, neuraminic acid, N-acetylglucosamine, fructose, mannose, fucose and other monosaccharides.

In eukaryotes, N-linked glycans are derived from a core 14-sugar unit assembled in the cytoplasm and endoplasmic reticulum. First, two N-acetyl glucosamine residues are attached to dolichol phosphate, a lipid, on the external side of the endoplasmic reticulum membrane. Five mannose residues are then added to this structure. At this point, the partially finished core glycan is flipped across the endoplasmic reticulum membrane, so that it is now located within the reticular lumen. Assembly then continues within the endoplasmic reticulum, with the addition of four more mannose residues. Finally, three glucose residues are added to this structure. Following full assembly, the glycan is transferred en bloc by the glycosyltransferase oligosaccharyltransferase to a nascent peptide chain, within the reticular lumen. This core structure of N-linked glycans thus consists of 14 residues (3 glucose, 9 mannose, and 2 N-acetylglucosamine).

In eukaryotes, O-linked glycans, are assembled one sugar at a time on a serine or threonine residue of a peptide chain in the Golgi apparatus. Unlike with N-linked glycans, there is as of yet no known consensus sequence. However, the placement of a proline residue at either −1 or +3 relative to the serine or threonine is favourable for O-linked glycosylation.

The first monosaccharide attached in the synthesis of O-linked glycans is N-acetyl-galactosamine. After this, several different pathways are possible. A Core 1 structure is generated by the addition of galactose. A Core 2 structure is generated by the addition of N-acetyl-glucosamine to the N-acetyl-galactosamine of the Core 1 structure. Core 3 structures are generated by the addition of a single N-acetyl-glucosamine to the original N-acetyl-galactosamine. Core 4 structures are generated by the addition of a second N-acetyl-glucosamine to the Core 3 structure. Other core structures are possible, though are less common.

A common structural theme in O-linked glycans is the addition of polylactosamine units to the various core structures. These are formed by the repetitive addition of galactose and N-acetyl-glucosamine units. Polylactosamine chains on O-linked glycans are often capped by the addition of a sialic acid residue (similar to neuraminic acid). If a fucose residue is also added, to the next to penultimate residue, a sialyl-lewis-X (SLex)) structure is formed.

The methods of the present invention may also be used to make conjugate vaccines, e.g. conjugate vaccines formed by linking one or more antigen molecules to a carrier protein, thereby conferring the immunological characteristics of the carrier protein on the antigen molecule. This approach is often used where the antigen molecule is a glycan group (e.g. an antigenic polysaccharide) as they tend to be comparatively poor antigens. The methods disclosed herein allow multiple antigen molecules to be attached to the carrier protein, preferably at one position on the protein carrier, through the use of the functionalising reagents of the present invention. Examples of conjugate vaccines include: *Haemophilus influenzae* type B vaccines ("Hib vaccine"), in which a Hib polysaccharide is conjugated to a protein carrier such as tetanospasmin, mutant diphtheria protein or meningococcal group B outer membrane protein; meningococcoal conjugates vaccines in which one or more meningococcal meningitis serogroup polysaccharides (e.g. A, C, Y or W-135) are conjugated to a protein carrier; pneumococcal polysaccharide vaccines (PPSV) in which the polysaccharides are cell membrane sugars from the different serotypes of pneumococcus (e.g. 1, 4, 5, 6B, 7F, 9V, 14, 18C, 19F, and 23F) conjugated with a carrier protein such as a Diphtheria proteins. The protein and polysaccharide components of any of the vaccines described above may be linked using the functionalising reagents of the present invention.

The methods disclosed herein can also be employed to engineer proteins containing other moieties useful for modifying the pharmacological properties of therapeutic proteins. One preferred example is the conjugation of polypeptides to poly(alkylene glycol) molecules, in particular polyethylene glycol (PEG) molecules, that may be used to enhance the half life or other pharmacological properties of polypeptide therapeutics. The present methods provide the opportunity to pegylate proteins of interest in a selective way depending on where the thiol groups are present in the protein. Poly(alkylene glycol) molecules are interchangeably referred to in the art as poly(alkylene oxide) molecules and are polyethers. Poly(alkylene glycol) molecules may have linear, branched, comb or star structures and generally are highly water soluble.

In addition, the basic poly(alkylene glycol) structure may be provided with one or more reactive functional groups such as hydroxy, amine, carboxylic acid, alkyl halide or thiol groups to facilitate the reaction of the poly(alkylene glycol) molecule with other species such as polypeptides. Preferred poly(alkylene glycol) molecules include those substituted at one or more hydroxyl positions with a chemical group, such as an alkyl group having between one and four carbon atoms. The most preferred poly(alkylene glycol) molecules for use in accordance with the present invention are polyethylene glycol ("PEG") molecules, although the skilled person would be able to use the techniques disclosed herein in conjunction with other poly(alkylene glycol) molecules, such as polypropylene glycol or polyethylene-polypropylene glycol copolymers. Poly(alkylene glycol) molecules, including PEGs, typically have molecular weights between about 400 Da and about 80 kDa, more preferably between about 1 kDa and about 60 kDa, and more preferably between about 5 kDa and about 50 kDa, e.g. molecular weights of 10 kDa, 20 kDa, 30 kDa or 40 kDa. Poly(alkylene glycol) molecules that may be used in accordance with the present invention are well known in the art and publicly available, for example from commercially available sources such as SigmaAldrich.

Pegylation is a known strategy for modifying the properties of therapeutic polypeptides, such as peptides, proteins and antibodies. In general, the attachment of PEG molecules to polypeptides is used to alter their conformation, electrostatic or hydrophobic properties, and lead to improvements in their biological and pharmacological properties, such as increasing drug solubility, reducing dosage frequency, modulating (especially increasing) circulating half-life, increasing drug stability and increasing resistance to proteolytic degradation Pegylation works by increasing the molecular weight of the therapeutic polypeptide by conjugating the polypeptide to one or more PEG polymer molecules. The methods of the present invention have the advantage that the site of introduction of the PEG molecules into a polypeptide is defined by the presence of thiol groups.

EXAMPLES

The following examples are set forth so as to provide those of ordinary skill in the art with a complete disclosure and description of how to practice the invention, and are not intended to limit the scope of the invention.

EXPERIMENTAL

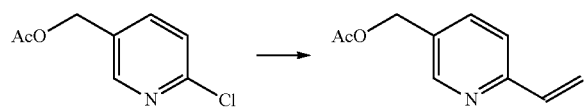

Tetrakis-(triphenylphosphine)palladium(0) (5 mol %, 62.3 mg) was added to a solution of (6-chloropyridin-3-yl)methyl acetate (200 mg) in DME (10 mL) and the solution left to stir at room temperature (20 min.). $K_2CO_3$ (0.16 g, 1.1 eq.), water (3 mL) and 2,4,6-trivinylcyclotriboroxane-pyridine complex (0.29 g, 1.1 eq.) were then added to the solution and the resultant mixture heated at reflux (24 hrs). The mixture was then cooled to room temperature and extracted with diethyl ether (100 mL) and the extract washed with water (30 mL). The diethyl ether extract was dried over $MgSO_4$ and then diluted with hexane (100 mL). The solution was filtered through aluminium oxide (2 g) and the eluent concentrated in vacuo to give a yellow oil. The oil was purified by silica gel chromatography (10-80% EtOAc/Pet ether) to yield (6-vinylpyridin-3-yl)methyl acetate as a colourless oil (172 mg, 90%). $^1$H NMR, 400 MHz (CDCl$_3$): 9.16 (d, 1H, H-6, J=2.3 Hz), 8.24 (dd, 1H, H-4, J=2.3 and 8 Hz), 7.39 (d, 1H, H-3, J=8 Hz), 6.85 (dd, 1H, H-A, J=11 and 17.6 Hz), 6.33 (dd, 1H, H-C, J=1.2 and 17.6 Hz), 5.61 (1H, H-B, J=1.2 and 11 Hz), 4.40 (m, 2H, —CH$_2$), 1.40 (m, 3H, —OCH$_3$). $^{13}$C NMR, 100 MHz (CDCl$_3$): 165.23, 159.07, 150.79, 137.56, 136.18, 124.72, 120.91, 120.62, 61.28, 14.25. ESI-HRMS Expected for $C_{10}H_{11}NO_2$=177.0790. Found M+H=178.0868.

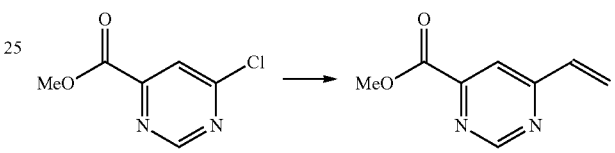

Tetrakis-(triphenylphosphine)palladium(0) (0.40 g, 5 mol %) was added to a solution of methyl 6-chloropyrimidine-4-carboxylate (1.24 g) in DME (35 mL) and the solution left to stir at room temperature (20 min.). $K_2CO_3$ (1.11 g, 1.2 eq.), water (10 mL) and 2,4,6-trivinylcyclotriboroxane-pyridine complex (1.93 g, 1.2 eq.) were then added to the solution and the resultant mixture heated at reflux (24 hrs). The mixture was then cooled to room temperature and extracted with diethyl ether (200 mL) and the extract washed with water (30 mL). The diethyl ether extract was dried over $MgSO_4$ and then diluted with hexane (200 mL). The solution was filtered through aluminium oxide (6 g) and the eluent concentrated in vacuo to give a yellow oil. The oil was then subjected to silica gel chromatography (10-100% EtOAc/Pet ether) followed by reverse phase (C18) chromatography (40% MeCN/water) to yield methyl 6-vinylpyrimidine-4-carboxylate as a white solid (0.40 g, 34% yield). $^1$H NMR, 270 MHz (CDCl$_3$): 9.29 (d, 1H, H-2, J=1.1 Hz), 7.99 (d, 1H, H-5, J=1.1 Hz), dd, 1H, H-A, J=10.4 and 17.3 Hz), 6.61 (dd, 1H, H-C, J=1.0 and 17.3 Hz), 5.81 (dd, 1H, H-B, J=1.0 and 10.4 Hz), 4.02 (s, 3H, —CH$_3$). $^{13}$C NMR, 67.5 MHz (CDCl$_3$): 164.79 (2C), 159.22 (2C), 134.71, 124.92, 117.71, 53.52. ESI-MS Expected for molecular ion $C_8H_8N_2O_2$=164.0586. Found M+H=165.0664.

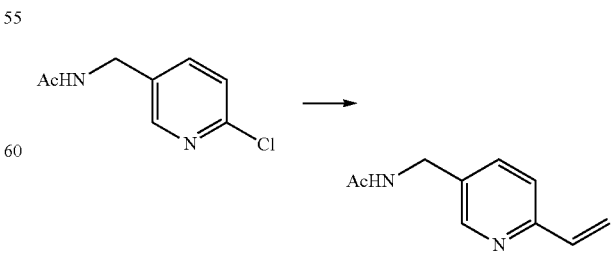

The above aryl halide (130 mg) was dissolved in 10 ml of DME, treated with tetrakis-(triphenylphosphine)palladium (0) (10 mol %, 81.38 mg). The solution was left to stir at room temperature for 20 minutes. $K_2CO_3$ (1.5 eq., 146 mg) was added along with water (3 ml) and 2,4,6-trivinylcyclotriboroxane-pyridine complex (1.5 eq., 254.24 mg). The reaction was refluxed for 24 hours. The reaction was allowed to cool to room temperature and diluted with diethyl ether (100 ml). This was washed with water (30 ml). The diethyl ether was dried over $MgSO_4$ and diluted with petroleum ether (100 ml). The solution was passed through a short aluminium oxide column. The solution was evaporated to dryness and the crude was purified initially by silica gel chromatography: 100% Pet ether to 10% MeOH/EtOAc to yield the above vinylpyridine compound as a yellow oil (89 mg, 72% yield). $^1$H NMR, 270 MHz (CDCl$_3$): 8.43 (s, 1H, H-6), 7.58 (dd, 1H, H-4, J=2.3 and 8 Hz), 7.29 (d, 1H, H-3, J=8 Hz). 6.78 (dd, 1H, H-A, J=10.7 and 17.4 Hz), 6.15 (dd, 1H, H-C, J=1.1 and 17.4 Hz), 6.06 (br. s, 1H, —NH), 5.46 (dd, 1H, H-B, J=1.1 and 10.7 Hz), 4.37 (d, 2H, —CH$_2$, J=5.8 Hz), 2.00 (s, 3H, —CH$_3$). $^{13}$C NMR, 67.5 MHz (CDCl$_3$): 170.16, 155.21, 148.96, 136.54, 136.34, 121.12, 118.45, 41.02, 23.29. ESI-MS Expected for molecular ion $C_{20}H_{22}N_2O$=176.0950. Found M+H=177.1028.

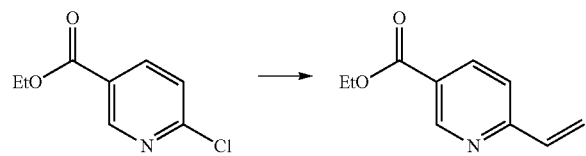

100 mg of the above aryl halide was dissolved in 5 ml of degassed, dry toluene. Tributyl(vinyl)tin (1.5 eq., 0.25 ml) and tetrakis-(triphenylphosphine)palladium(0) (5 mol %, 34 mg) was added. The reaction was refluxed, under nitrogen for 1 hour. The reaction was left to cool to room temperature and diluted with 50 ml of toluene. The reaction was filtered through a 1:1 mixture of celite and KF powder. The filtrate was concentrated. The crude was resuspended on 50 ml of EtOAc and washed with (1) water and (2) sat. NaCl soln. The EtOAc was dried over $MgSO_4$, filtered and concentrated. The crude was purified by silica gel/KF (10% w/w) chromatography: 10% EtOAc/Pet ether to 60% EtOAc/Pet ether to yield the above vinyl pyridine compound as pure white crystals (31 mg, 33% yield). $^1$H NMR, 270 MHz (CDCl$_3$): 8.56 (d, 1H, H-6, J=2 Hz), 7.65 (dd, 1H, H-4, J=2 and 8 Hz), 7.34 (d, 1H, H-3, J=8 Hz), 6.81 (dd, 1H, H-A, J=11 and 17.3 Hz), 6.20 (dd, 1H, H-C, J=1.4 and 17.3 Hz), 5.50 (dd, 1H, H-B, J=1.4 and 11 Hz), 5.10 (s, 2H, —CH$_2$), 2.10 (s, 3H, —OCH$_3$). $^{13}$C NMR, 67.5 MHz (CDCl$_3$): 167.9, 149.62, 136.77, 136.56, 130.30, 120.96, 118.83, 63.70, 21.00. ESI-HR MS Expected for $C_{10}H_{11}NO_2$=177.0790; Found M+H=178.0859.

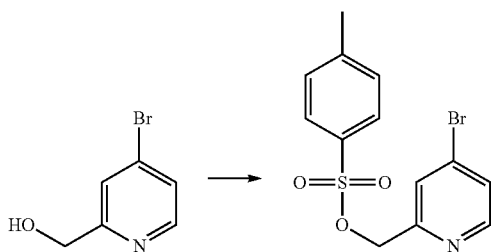 [SMILES: OCc1cc(Br)ccn1 ; Cc1ccc(S(=O)(=O)OCc2cc(Br)ccn2)cc1]

(4-bromopyridin-2-yl)methanol (100 mg, 0.53 mmol) was dissolved in dry THF (10 ml) and cooled to 0° C. Tosyl chloride (2 eq., 202.8 mg, 1.06 mmol) and 1M NaOH (0.7 ml) was added and the reaction was rapidly stirred for 2 hours while being allowed to warm to room temperature. The reaction was concentrated then resuspended in 100 ml of dichloromethane. This was extracted with water and brine. The dichloromethane was dried over magnesium sulphate, filtered and concentrated. The crude was purified by silica gel chromatography: 10%-50% ethyl acetate/petroleum ether to yield a yellow oil (171 mg, 94%). $^1$H NMR, 270 MHz (CDCl$_3$): 8.30 (d, 1H, J=5.5 Hz), 7.81 (app. d, 2H), 7.53 (dd, 1H, J=0.5 and 1.9 Hz), 7.35-7.31 (m, 3H), 5.10 (s, 2H), 2.43 (s, 3H). $^{13}$C NMR, 67.5 MHz (CDCl$_3$): 155.4, 150.0, 145.4, 133.9, 130.1, 128.2, 126.8, 125.2, 70.9, 21.8. ESI-MS: Expected for $C_{23}H_{22}Br_1N_2O_3S_2$=340.9721 and 342.9701. Found M+H=341.9790 and 343.9770.

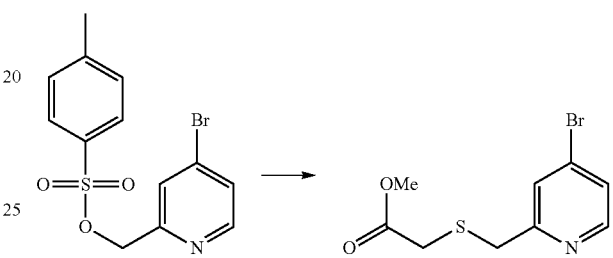

(4-bromopyridin-2-yl)methyl 4-methylbenzenesulfonate (170 mg, 0.50 mmol) was dissolved in dry DMF (10 ml). Caesium carbonate (2 eq., 325.7 mg, 1.00 mmol) and methyl thioglycolate (5 eq., 2.50 mmol, v=0.23 ml) were added and the reaction was stirred rapidly under nitrogen at room temperature for 3 hours. The reaction was concentrated then resuspended in dichloromethane. This was extracted with water and brine. The dichloromethane was dried over magnesium sulphate, filtered and concentrated. The crude was purified by silica gel chromatography: 10%-50% ethyl acetate/petroleum ether to yield a yellow oil (99.4 mg, 72%). $^1$H NMR, 270 MHz (CDCl$_3$): 8.35 (d, 1H, J=5.2 Hz), 7.54 (d, 1H, J=2.0 Hz), 7.34 (dd, 1H, J=1.9 and 5.2 Hz), 3.90 (s, 2H), 3.70 (s, 3H), 3.22 (s, 2H). $^{13}$C NMR, 67.5 MHz (CDCl$_3$): 170.6, 159.4, 150.3, 133.5, 126.6, 125.7, 52.6, 37.9, 32.8. ESI-MS: Expected for $C_9H_{10}Br_1N_1O_2S_1$=274.9616 and 276.9595. Found M+H=275.9691 and 277.9667.

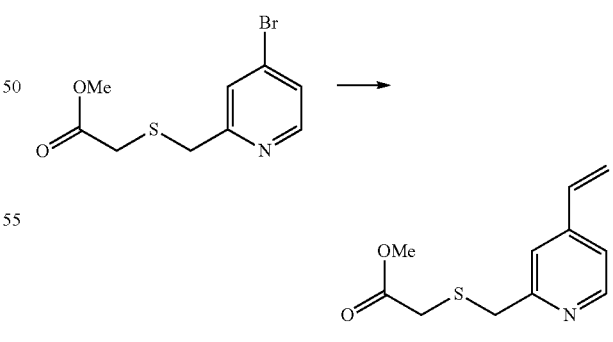

Methyl 2-((4-bromopyridin-2-yl)methylthio)acetate (0.62 g, 2.25 mmol) was dissolved in dry, deoxygenated toluene. Palladium tetrakis (10 mol %, 259.6 mg, 0.22 mmol) and tributyl(vinyl)tin (1.8 eq., v=1.18 ml) were added and the reaction was refluxed under nitrogen for 2 hours. The reaction was allowed to cool then purified by silica gel chromatography (containing 10% w/w potassium fluoride): 10%-50% ethyl acetate/petroleum ether to yield a yellow oil (416 mg, 83%). $^1$H NMR, 270 MHz (CDCl$_3$): 8.47 (d, 1H, J=5.3 Hz), 7.31 (s, 1H), 7.15 (dd, 1H, J=1.6 and 5.3 Hz), 6.63 (dd, 1H, J=10.7 and 17.6 Hz), 5.96 (d, 1H, J=17.6 Hz), 5.48 (d, 1H, J=10.7 Hz), 3.92 (s, 2H), 3.69 (s, 3H), 3.21 (s, 2H). ESI-MS: Expected for C$_{11}$H$_{13}$N$_1$O$_2$S$_1$=223.0667. Found M+H=224.0720.

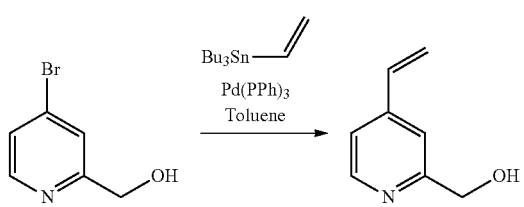

A stirring solution of compound I (59 mg, 0.32 mmol), tributyl(vinyl)tin (0.187 mL, 0.64 mmol) and palladium tetrakis (37 mg, 0.032 mmol) in dry toluene was deoxygenated under argon at room temperature. The mixture was then refluxed for 2 hours under argon before being allowed to cool to room temperature. The mixture was filtered through celite and concentrated in vacuo before purification via flash chromatography (50% EtOAc/Pet. ether to 100% EtOAc) afforded 37 mg of product as a clear oil (85% yield). $^1$H NMR, 270 MHz (CDCl$_3$): 8.46 (d, 1H, J=4.5 Hz), 7.19 (dd, 2H, J=4.5 and 16.6 Hz), 6.65 (dd, 1H, J=10.7 and 17.6 Hz), 5.96 (d, 1H, J=17.6) 5.48 (d, 1H, J=10.7), 4.74 (s, 2H). ESI-MS: Expected for C$_8$H$_9$O$_1$N$_1$=135.0684. Found M+H=136.0760.

20 mg of glutathione (reduced form) was dissolved in 2 ml of water. 2-vinyl pyridine (1.2 eq., 6.3 µl) was added. The reaction was sonicated for one minute then left to stir for two hours at room temperature. The cloudy solution eventually becomes transparent. The reaction was concentrated to dryness, resuspended in MeOH (10 ml) and dry-packed onto silica gel. This was loaded onto a silica gel column for purification; 100% EtOAc to 50% (10% NH$_3$/MeOH)/EtOAc to yield product as a white powder (23 mg, 86% yield). $^1$H NMR, 400 MHz (D$_2$O): 8.29 (dd, 1H, H-18, J=0.8 and 5.1 Hz), 7.66 (ddd, H-20, J=2.0, 7.8 and 15.7 Hz), 7.23 (d, 1H, H-21, J=7.8 Hz), 7.18 (ddd, 1H, H-19, J=0.8, 5.1 and 7.8 Hz), 4.37 (dd, 1H, H-7, J=4.7 and 9.0 Hz), 3.60 (m, 3H, H-2 and H-10), 2.87 (m, 5-H, H-12$_A$, H-14$_A$ and H-14$_B$, H-15$_A$ and H-15$_B$), 2.65 (dd, 1H, H-12$_B$, J=9.0 and 14.1 Hz), 2.34 (m, 2H, H-4$_A$ and H-$_B$), 1.92 (m, 2H, H-3$_A$ and H-3$_B$). $^{13}$C NMR, 100 MHz (D$_2$O): 176.29, 174.96, 174.20, 172.01, 159.09, 148.36, 138.23, 124.26, 122.48, 54.21, 53.10, 43.43, 36.57, 32.98, 31.50, 31.48, 26.40. ESI-MS Expected for molecular ion C$_{17}$H$_{24}$N$_4$O$_6$S=412.1417. Found M+H=413.1447.

20 mg of glutathione (reduced form) was dissolved in 2 ml of water. 2-vinyl pyridine (1.2 eq., 6.3 µl) was added. The reaction was sonicated for one minute then left to stir for two hours at room temperature. The cloudy solution eventually becomes transparent. The reaction was concentrated to dryness, resuspended in MeOH (10 ml) and dry-packed onto silica gel. This was loaded onto a silica gel column for purification; 100% EtOAc to 50% (10% NH$_3$/MeOH)/EtOAc to yield product as a white powder (21 mg, 78% yield). $^1$H NMR, 400 MHz (D$_2$O): 7.65 (dd, 2H, H-18 and H-20, J=1.6 and 5.1 Hz), 6.63 (d, 2H, H-17 and H-21, J=6.3 Hz), 3.74 (dd, 1H, H-7, J=4.7 and 9.0 Hz), 2.94 m, 3H, H-2, H-10$_A$ and H-10$_B$), 2.29-2.01 (m, 6H, H-12$_A$, H-12$_B$, H-14$_A$ and H-14$_B$, H-15$_A$ and H-15$_B$), 1.69, (t, 2H, H-4$_A$ and H-4$_B$), 1.32 (q, 2H, H-3$_A$ and H-3$_B$). $^{13}$C NMR, 100 MHz (D$_2$O): 175.67, 174.35, 173.44, 171.39, 152.15, 146.75, 124.62, 53.56, 52.47, 42.81, 33.69, 32.35, 30.88, 25.70. ESI-MS Expected for molecular ion C$_{17}$H$_{24}$N$_4$O$_6$S=412.1417. Found M+H=413.1495

Results: All reactions performed in TRIS-based buffer at pH 7.5 unless stated otherwise.

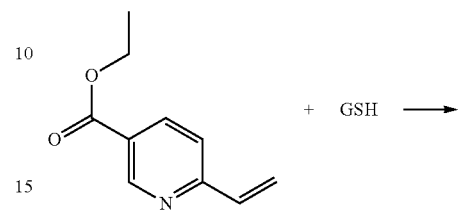

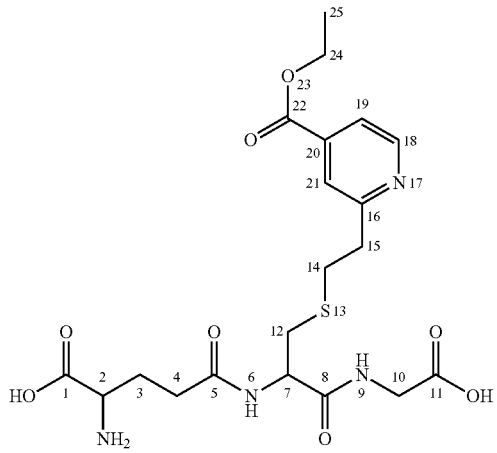

Chemical Formula: C$_{20}$H$_{28}$N$_4$O$_8$S
Exact Mass: 484.1628
Molecular Weight: 484.5233

The ethyl ester (43.2 mg) was added to a solution of reduced glutathione (15 mg) and TCEP (10 mM) in deoxygenated water (2 ml). The reaction was left to stir under N$_2$ for 48 hours. The reaction was concentrated, dry-packed onto silica, and loaded onto a silica gel column. The product was purified by 1:4 (10% NH$_3$/MeOH)/EtOAc (16 mg, 68% yield). $^1$H NMR, 400 MHz (D$_2$O): 9.00 (d, 1H, H-18, J=2.0 Hz), 8.45 (dd, 1H, H-20, J=2.0 and 8.2 Hz), 7.60 (d, 1H, H-21, J=8.2 Hz), 4.43 (dd, 1H, H-7, J=5.1 and 8.6 Hz), 4.35 (q, 2H, H-24$_A$ and H-24$_B$, J=7.0 Hz), 3.78 (s, 2H, H-10), 3.67 (app. t, 1H, H-2, J=6.7 Hz), 3.16 (m, 2H, H-15$_A$ and H-15$_B$), 2.93 (m, 3H, H-12$_A$, H-14$_A$ and H-14$_B$), 2.75 (dd, 1H, H-12$_B$, J=8.6 and 13.6 Hz), 2.40 (app. t, 2H, H-4), 2.03 (m, 2H, H-3), 1.30 (t, 3H, H-25, J=7.0 Hz). $^{13}$C NMR, 100 MHz (D$_2$O): 174.76, 174.41, 173.74, 172.28, 165.94, 162.25, 147.21, 141.02, 125.74, 125.22, 62.88, 53.91, 52.95, 42.13, 35.57, 32.77, 31.24, 30.66, 26.05, 13.28. ESI-MS Expected for molecular ion C$_{20}$H$_{28}$N$_4$O$_8$S=484.1628. Found M−H=483.2047.

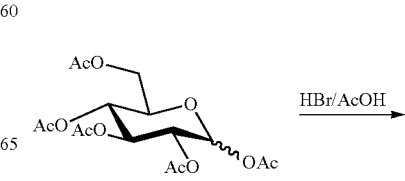

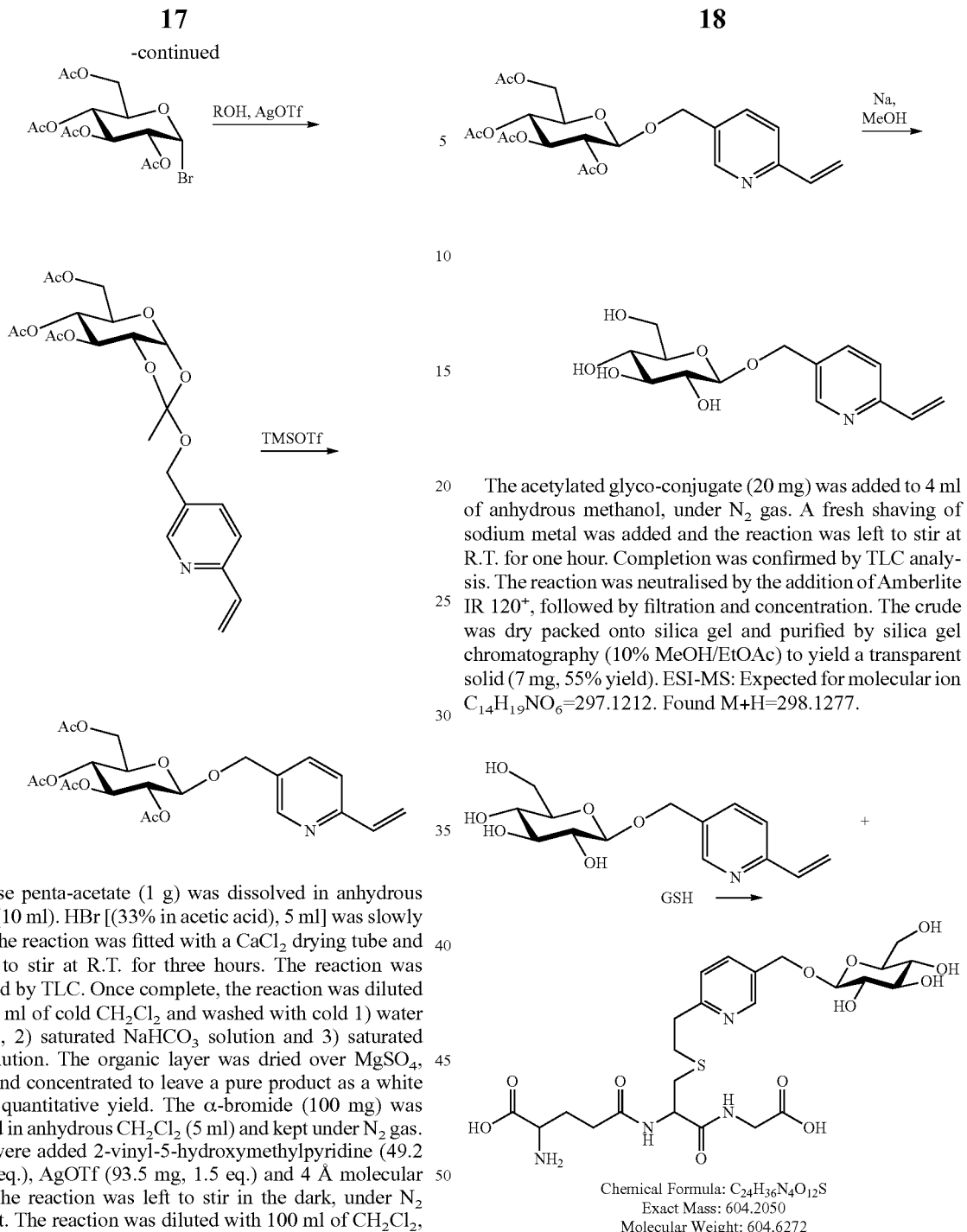

Glucose penta-acetate (1 g) was dissolved in anhydrous CH$_2$Cl$_2$ (10 ml). HBr [(33% in acetic acid), 5 ml] was slowly added. The reaction was fitted with a CaCl$_2$ drying tube and was left to stir at R.T. for three hours. The reaction was monitored by TLC. Once complete, the reaction was diluted with 100 ml of cold CH$_2$Cl$_2$ and washed with cold 1) water (100 ml), 2) saturated NaHCO$_3$ solution and 3) saturated NaCl solution. The organic layer was dried over MgSO$_4$, filtered and concentrated to leave a pure product as a white foam in quantitative yield. The α-bromide (100 mg) was dissolved in anhydrous CH$_2$Cl$_2$ (5 ml) and kept under N$_2$ gas. To this were added 2-vinyl-5-hydroxymethylpyridine (49.2 mg, 1.5 eq.), AgOTf (93.5 mg, 1.5 eq.) and 4 Å molecular sieves. The reaction was left to stir in the dark, under N$_2$ overnight. The reaction was diluted with 100 ml of CH$_2$Cl$_2$, filtered through celite, then washed with 1) saturated NaHCO$_3$ solution and 2) saturated NaCl solution. The organic layer was dried over MgSO$_4$, filtered and concentrated. The crude material was purified by silica gel chromatography (10% EtOAc/Pet. Ether to 100% EtOAc, to yield the ortho ester (82 mg, 73%). The ortho ester (73 mg) was dissolved in 5 ml of anhydrous CH$_2$Cl$_2$ and cooled to −20° C., while kept under N$_2$ gas. TMSOTf (5.7 μl, 0.2 eq.) was slowly added and the reaction was carefully monitored over one hour by TLC analysis. Upon completion, the reaction was quenched by the addition of two drops of Et$_3$N. The reaction was concentrated and purified by silica gel chromatography to yield the glyco-conjugate (23 mg, 32% yield). ESI-MS: Expected for molecular ion C$_{22}$H$_{27}$NO$_{20}$=465.1635. Found M+H=466.1718.

The acetylated glyco-conjugate (20 mg) was added to 4 ml of anhydrous methanol, under N$_2$ gas. A fresh shaving of sodium metal was added and the reaction was left to stir at R.T. for one hour. Completion was confirmed by TLC analysis. The reaction was neutralised by the addition of Amberlite IR 120$^+$, followed by filtration and concentration. The crude was dry packed onto silica gel and purified by silica gel chromatography (10% MeOH/EtOAc) to yield a transparent solid (7 mg, 55% yield). ESI-MS: Expected for molecular ion C$_{14}$H$_{19}$NO$_6$=297.1212. Found M+H=298.1277.

The glycol-conjugate (2 mg) was dissolved in 180 μl of deoxygenated water, containing 10 mM TCEP. Glutathione (reduced form, 3.1 mg, 1.2 eq) was added and the reaction was left to stir at R.T overnight. Mass spectrometry confirmed the presence of product. ESI-MS: Expected for molecular ion C$_{24}$H$_{36}$N$_4$O$_{12}$S=604.2050. Found M−H=603.1955.

This example confirms that the compounds and methods of the present invention may be employed to covalently conjugate a polypeptide to a glycan group. The example also shows that the reaction is specific for the thiol group present in glutathione and that side reactions with other functional groups such as amines and carboxylic acids do not occur.

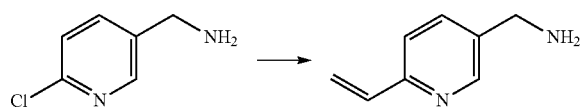

The above aryl halide (0.5 g) was dissolved in 12 ml of DME and treated with tetrakis-(triphenylphosphine)palladium(0) (10 mol %, 0.41 g). The solution was left to stir at room temperature for 20 minutes. $K_2CO_3$ (1.5 eq., 0.73 g) was added along with water (3 ml) and 2,4,6-trivinylcyclotriboroxane-pyridine complex (1.5 eq., 1.27 g). The reaction was refluxed for 24 hours. The reaction was allowed to cool to room temperature then filtered through celite. The reaction mixture was concentrated then resuspended in 200 ml of EtOAc. This was washed with water (2×100 ml). The water washes were pooled and concentrated down to 5 ml. The concentrate was loaded onto a C-18 reverse phase column and eluted with 1/10 MeOH/$H_2O$. The relevant fractions were pooled and freeze-dried to yield the product as a white solid (188 mg, 40% yield). ESI-MS: Expected for molecular ion $C_8H_{10}N_2$=134.0844. Found M+H=135.0922.

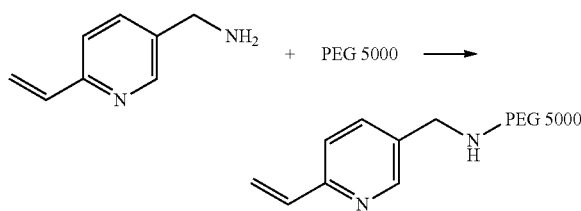

The mPEG-5K-COOH (100 mg) was co-evaporated with anhydrous toluene (3×25 ml) then left on the high-vacuum pump to dry for 2 hours. Subsequently, the PEG was dissolved in 5 ml of anhydrous DMF, while under inert conditions. The aromatic-amine (13.4 mg, 5 eq.), PyBOP (52.1 mg, 5 eq.) and DIPEA (0.05 ml) were added. The reaction was left to stir under $N_2$ gas, at 30° C. overnight. The reaction was then concentrated and co-evaporated with toluene (4×25 ml). The crude material was suspended in warm ethanol then left in −20° C. freezer for one hour, which resulted in the precipitation of the PEG-conjugate. The mixture was filtered and washed with cold ethanol. The white, waxy product (31 mg) was left to dry on a high-vacuum pump for two hours.

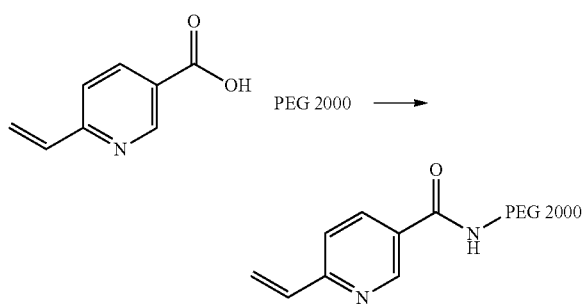

The mPEG-2K-$NH_2$ (100 mg) was co-evaporated with anhydrous toluene (3×25 ml) then left on the high-vacuum pump to dry for 2 hours. Subsequently, the PEG was dissolved in 5 ml of anhydrous DMF, while under inert conditions. The aromatic-amine (37.3 mg, 5 eq.), PyBOP (130.1 mg, 5 eq.) and DIPEA (0.05 ml) were added. The reaction was left to stir under $N_2$ gas, at 30° C. overnight. The reaction was then concentrated and co-evaporated with toluene (4×25 ml). The crude material was suspended in $CH_2Cl_2$ and purified by silica gel chromatography (100% $CH_2Cl_2$ to 15% MeOH/$CH_2Cl_2$). The relevant fractions were pooled and concentrated to afford the product as a transparent solid (52 mg).

These examples confirm that the compounds and methods of the present invention may be employed to covalently conjugate a polypeptide to a PEG molecules in a specific manner.
Relative Rates of Reaction of a Range of Linkers with Glutathione.

A solution of the vinyl pyridine or vinyl pyrimidine (1.2 eq.) in 200 µl of deuterated DMSO was added to a solution of reduced glutathione (6-10 mg) in $D_2O$ (800 µl) at pH 7.0 in an NMR tube. Once mixed, the tube was quickly transferred to the NMR spectrometer. The lock and shims were readjusted (1-2 mins). Spectra were continually acquired over the designated reaction time (16-32) scans per data point, on a Varian Mercury (400 MHz) Spectrometer. Relative reaction rates were determined by measuring the loss in intensity of signal from the vinyl protons (δ 6.6-6.9 ppm) over time.
Labelling of Human Recombinant IFN-Beta with Vinylpyridine-PEG Derivative Versus Maleimide-PEG A reaction was carried out to compare labelling of the polypeptide interferon beta with a PEG-pyridine conjugate according to the present invention and the use of PEG and the prior art cross-linking agent maleimide. Recombinant interferon beta (C17S, D80N) reacted with PEG-pyridine or PEG Maleimide. Human interferon beta-1, fibroblast (Origene Technologies) mutated at C17S to remove endogenous free cysteine and D80C to replace endogenous glycosylation site by site directed mutagenesis (Stragene Quickchange). Recombinant interferon beta reduced with 0.1 mM TECP for 12 h followed by reaction with PEG/pyridine or PEG/maleimide at time point specified in diagram at pH 7.5, 37° C. Proteins were resolved using SDS-PAGE and were transferred onto nitrocellulose membrane. Membranes were probed with anti-interferon b antibody for unreacted and Pegylated IFNb. Secondary antibody reaction detected using ECL detection system (Amershan, GE Healthcare).

Figure 2:
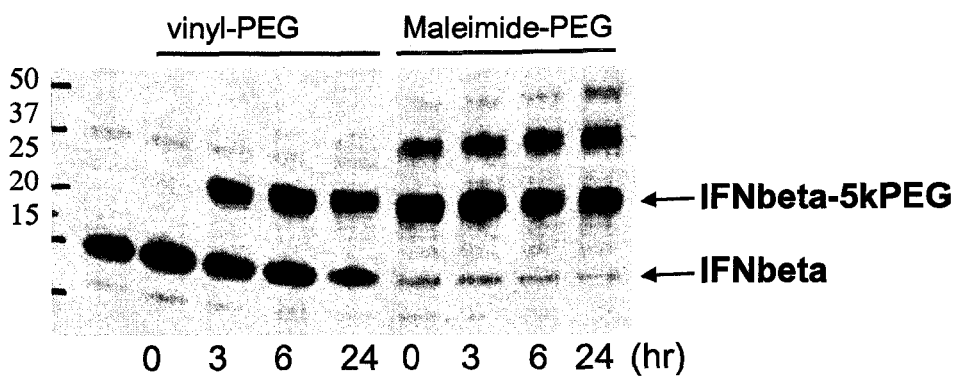
FIG. 2. Labelling of human recombinant interferon-beta with vinylpyridine-PEG derivative versus maleimide-PEG.

In both cases, the PEG molecule had a molecular weight of 5 kD. The results are shown in FIG. 2 and show that the use of the conjugate of the present invention coupled an average of one PEG-conjugate to the interferon beta, with molecular weight increasing from approx. 20 kD to 25 kD, increasing over reaction time. In contrast, the reaction with maleimide was significantly less specific and led to the conjugation of multiple PEG molecules to the interferon beta.
Effect of pH on Rate of Labelling of BSA with Vinylpyridine-5k-PEG pH dependence of bovine serum albumin (Sigma) functionalized with 5 kD PEG/pyridine was investigated. BSA reduced with 1 mM DTT at 4° C. for 12 h followed by reaction with 5 kD PEG/pyridine at room temperature at the time indicated. Proteins resolved by SDS-PAGE and stained with Commassie blue for visualization.

Figure 3:
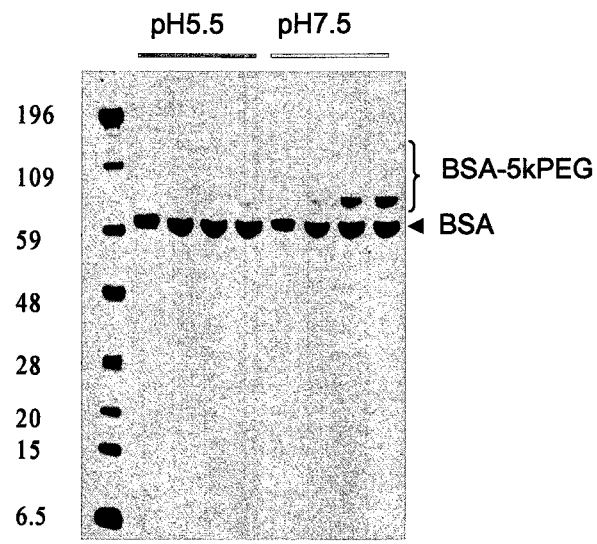
FIG. 3. Effect of pH on rate of labelling of BSA with vinylpyridine-5k-PEG

The results in FIG. 3 were obtained at pH 5.5 and 7.5 and show that the conjugation reaction proceeds at both pHs, but is faster at pH 7.5. This has been confirmed in other experiments that show that the reaction can be used over a wide range of pH, including the range of physiological pH relevant to protein biochemistry. The results also show that pH may be used to control the rate of the conjugation reaction.
Temperature Dependence of 5 kD PEG/Pyridine Reaction with Recombinant IFN Beta (C17S, N80C).

Figure 4:
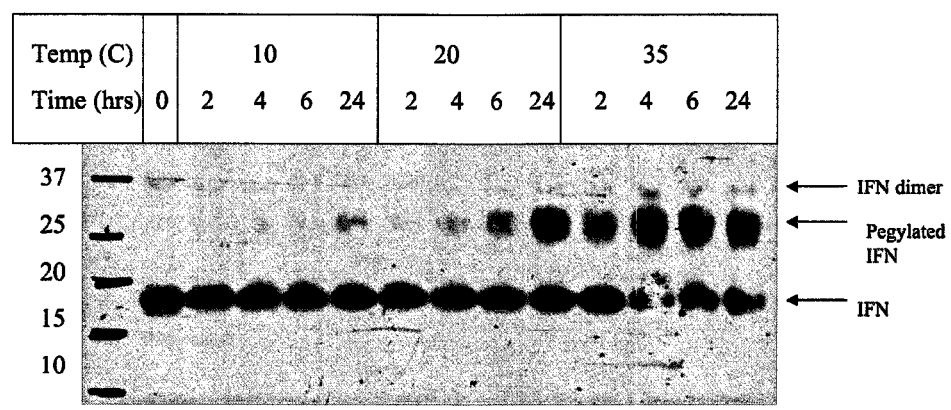
FIG. 4. Temperature dependence of 5 kDa PEG/pyridine reaction with recombinant IFN beta (C17S, D80N).

IFN beta mutant was treated with 5 mM 5 kDa PEG vinyl pyridine reagent at pH 7, at temperatures indicated. Aliquots were taken at time points indicated and the reaction quenched by addition of DTT. Proteins were resolved using SDS-PAGE and were transferred onto nitrocellulose membrane. Membranes were probed with anti-interferon beta antibody for unreacted and Pegylated IFN-beta. Secondary antibody reaction detected using ECL detection system (Amershan, GE Healthcare). The results are presented in FIG. 4.

Protein Functionalisation Reactions

Reaction Conditions

The protein was diluted (5 mg/ml) in deoxygenated reaction buffer (NaC$_2$H$_3$O, 20 mM, pH 5.5) and reduced under nitrogen for 3 hours with either tris-(carboxyethyl)-phosphine hydrochloride (TCEP, 5 mM) or β-mercaptoethylamine (BMEA, 5 mM). Excess reducing agent was subsequently removed either by three rounds of ultrafiltration (Milipore centricons 10 kDa cut-off) or two rounds of dialysis (cellulose acetate membrane, 6-8 kDa cut-off). A 10-fold solution of PEG in the reaction buffer was prepared and added to the protein solution to give the reaction mixture containing protein (1 mg/ml) plus 1.5 to 5 molar equivalents of PEG as required. The mixture was incubated in a sealed tube overnight (37° C.).

FPLC

The reaction mixture was diluted 5 to 10-fold with 10 mM NaC$_2$H$_3$O, pH 4.5. The sample was loaded onto a SP-sepharose cation exchange column pre-equilibrated with 3 column volumes of binding buffer (10 mM NaC$_2$H$_3$O, pH 4.5). After being washed to remove the nonbound fractions (3 column volumes of binding buffer) the protein was eluted with a linear salt gradient (50-200 mM NaCl, 10 mM NaC$_2$H$_3$O, pH 4.5), and 1.5 mL fractions were collected. Fractions containing the protein were analysed by gel electrophoresis.

SDS PAGE Analysis

The degree of PEGylation of the protein was assessed by gel electrophoresis. Typically protein samples (1-10 μg) were diluted with loading dye containing 1 mM dithiothreitol (DTT) and boiled for 3 minutes to denature prior to loading onto a NUPAGE BisTris 4-12% gel (Invitrogen). Coomassie Stain was used to detect protein (blue) and Dragendorff (iodobismuthate) to visualize polyethylene glycols (orange-brown).

Functionalisation of Model Protein with PermaLink

Figure 5:
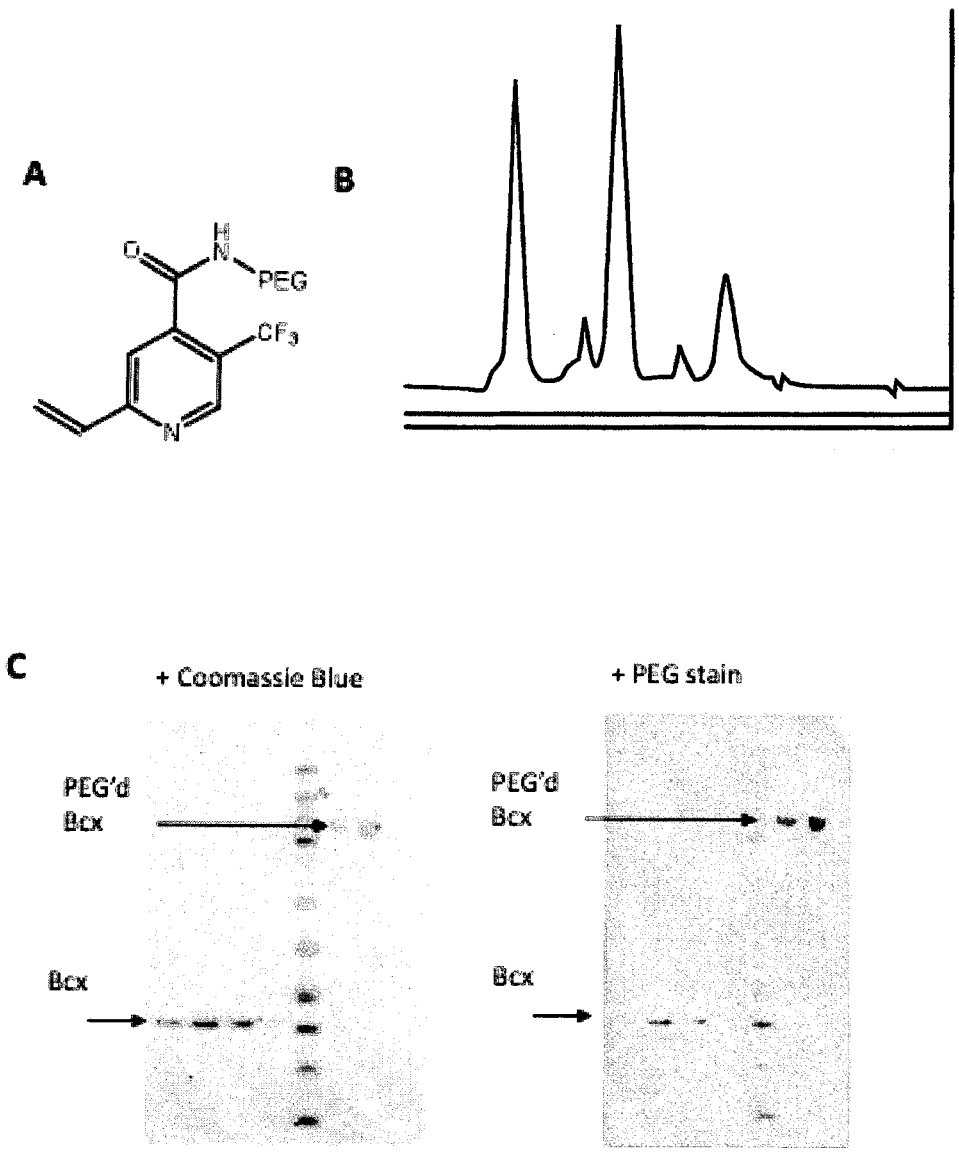
FIG. 5. Functionalization of model protein with Perma-Link.

A model protein, *Bacillus circulans* xylanase (S22C) mutant (BcxS22C), was chosen to illustrate how polypeptides can be functionalized with glycan or PEG molecules in accordance with the present invention using the Permalink functionalising reagents. Details of the experiments are set out in FIG. 5 which shows: (A) Structure of PL-LK-07. (B) A solution of BcxS22C (5 mg/ml) in deoxygenated sodium acetate buffer (20 mM, pH 5.5) was reduced for 3 hours with tris-(carboxyethyl)-phosphine hydrochloride (TCEP, 5 mM). Excess reducing agent was subsequently removed by three rounds of ultrafiltration (Milipore centricons 10 kDa cut-off). The PEG (1.5 eq) was added to the protein solution (1 mg/ml) and incubated overnight (37° C.). PEGylated protein was recovered from the reaction mixture via liquid chromatography using a sepharose SP cation exchange column. The sample was diluted five-fold and loaded onto the column pre-equilibrated in binding buffer (10 mM sodium acetate, pH 4.5). The product was eluted with a linear salt gradient (50-200 mM NaCl in binding buffer) and 1.5 ml fractions were collected. (C) Fractions containing protein as depicted by UV absorbance at 280 nm were analysed by SDS PAGE. This shows that vinylpyridine compounds are effective reagents for the attachment of polyethyleneglycol (PEG) to cysteine residues of proteins, and that the products of such reactions can be obtained in high purity.

Figure 6:
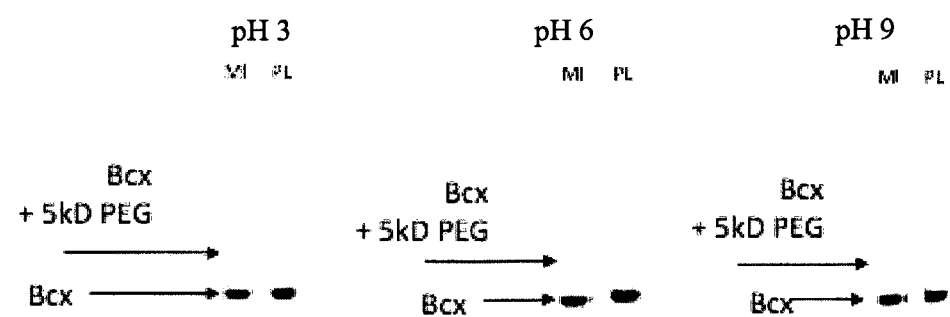
FIG. 6. Specificity of the linker for cysteine residues.

Specificity of the Functionalising Reagent for the Thiol Groups of Cysteine Residues As one of the disadvantages of maleimide based linker chemistry is a lack of reaction specificity, the functionalising reagents of the present invention were tested to determine their specificity for cysteine residues and the results are reported in FIG. 6. To gauge the specificity of the linker for cysteine residues a sample of wild type Bcx with no cysteines present was used. This protein was first reduced with tris-(carboxyethyl)-phosphine hydrochloride (TCEP, 5 mM) in sodium acetate buffer (20 mM, pH 5.5) for 3 hours. After this time any remaining reducing agent was removed by three rounds of ultrafiltration (Milipore centricons 10 kDa cut-off). The resulting concentrated protein solution was diluted to 1.2 mg/ml in the relevant buffer (50 mM, citrate buffer pH3, acetate buffer pH6, tris buffer pH9). A solution of the PEG (5 eq) was added to the protein to give a final protein concentration of 1 mg/ml. The reactions were incubated overnight (16 hours, 37° C.). The amount of PEGylated product was calculated by running reaction samples on a 4-12% SDS PAGE. This shows that vinylpyridine reagents display greater specificity towards the sulfhydryl group of cysteine residues over other amino acids, compared to maleimide reagents.

All publications, patent and patent applications cited herein or filed with this application, including references filed as part of an Information Disclosure Statement are incorporated by reference in their entirety.

The invention claimed is:

1. A compound represented by formula:

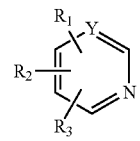

wherein:

X and Y are independently selected from CH or N;

wherein at least $R_1$, and optionally $R_2$, are covalently linked to a poly(alkylene glycol) molecule and/or a glycan group;

wherein $R_1$, and optionally $R_2$, are independently selected from:
- —(CH$_2$)$_n$—Z—(CH$_2$)$_o$—R, where Z is O, S or NH, n is 0 to 10, o is 0 to 10 and where R is a hydrogen, a poly(alkylene glycol) molecule or a glycan group, or
- —C(O)—Z—(CH$_2$)$_o$—R, Z is O, S or NH, o is 0 to 10 and where R is a hydrogen, a poly(alkylene glycol) molecule or a glycan group; or
- —(CH$_2$)$_n$—Z—C(O)—(CH$_2$)$_o$—R, where Z is O, S or NH, n is 0 to 10, o is 0 to 10 and where R is a hydrogen, a poly(alkylene glycol) molecule or a glycan group; or
- —Y—(CH$_2$)$_n$—Z—C(O)—(CH$_2$)$_o$—R, where Y is an aryl group, O, S or NH, Z is O or NH, n is 0 to 10, o is 0 to 10 and where R is a hydrogen, a poly(alkylene glycol) molecule or a glycan group; or
- —Y—R, where Y is O or S, R is a hydrogen, a glycan, a poly(alkylene glycol) molecule, aryl or C$_{1-10}$ alkyl;

with the proviso that when $R_2$ is not linked to a poly(alkylene glycol) molecule or a glycan group, it may additionally be selected from hydrogen or an electron withdrawing group, such as halogen (F, Cl, or Br), —NO$_2$, —CO$_2$H, —CO$_2$R$_4$, COR$_4$, —CHO, —CN, —CF$_3$, —SO$_2$NR$_4$R$_5$, alkyl or phenyl, where R$_4$ and R$_5$ are independently selected from hydrogen or C$_{1-10}$ alkyl;

or R$_2$ and R$_3$ together form a fused (hetero) aromatic ring substituent which may include, but is not limited to, an indole, indazole, benzimidazole, quinoline, isoquinoline, aziradine or a purine;

or R$_3$ is selected from hydrogen or a substituent selected from halo, hydroxy, ether, formyl, acyl, carboxy, ester, acyloxy, amido, acylamido, thioamido, tetrazolyl, amino, nitro, nitroso, azido, cyano isocyano, cyanato, isocyanato, thiocyano, isothiocyano, thioether, sulfonic acid, sulfonate, sulfone, sulfonyloxy, sulfinyloxy, sulfamino, sulfonamino, sulfinamino, sulfamyl, sulfonamido, C$_{1-7}$ alkyl.

2. The compound of claim 1, wherein X and Y are both CH or one of X and Y is CH and the other is N.

3. The compound of claim 1, wherein the poly(alkylene glycol) molecule is a polyethylene glycol.

4. The compound of claim 1, wherein one of R$_1$ or R$_2$ comprises a poly(alkylene glycol) molecule or a glycan group.

5. The compound of claim 1, wherein R$_1$ and R$_2$ comprise a poly(alkylene glycol) molecule and/or a glycan group.

6. The compound of claim 1, wherein one of R$_1$ and R$_2$ comprises a poly(alkylene glycol) molecule and the other of R$_1$ and R$_2$ comprises a glycan group.

7. The compound claim 1, wherein the R$_1$ and/or R$_2$ groups for linking the poly(alkylene glycol) molecule and/or the glycan group to the nitrogen containing heterocyclic aromatic ring are independently selected from —(CH$_2$)n-Z—(CH$_2$)$_o$—R or —C(O)—Z—(CH$_2$)$_o$—R.

8. The compound of claim 1, wherein in the R$_1$ and R$_2$ in said formula represent —(CH$_2$)$_n$—Z—R or —C(O)—Z—R.

9. A conjugate formed by the reaction of a compound according to claim 1 and one or more thiol groups of a polypeptide.

10. A compound represented by one of the general formulae:

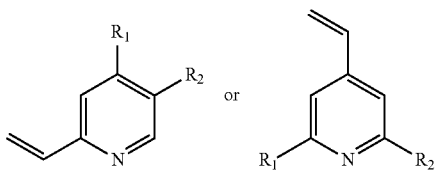

wherein:

at least R$_1$, and optionally R$_2$, are covalently linked to a poly(alkylene glycol) molecule and/or a glycan group;

and further wherein:

R$_1$, and optionally R$_2$, are independently selected from:
- —(CH$_2$)$_n$—Z—(CH$_2$)$_o$—R, where Z is O, S or NH, n is 0 to 10, o is 0 to 10 and where R is a hydrogen, a poly(alkylene glycol) molecule or a glycan group, or
- —C(O)$_n$—Z—(CH$_2$)$_o$—R, Z is O, S or NH, o is 0 to 10 and where R is a hydrogen, a poly(alkylene glycol) molecule or a glycan group, or
- —(CH$_2$)$_n$—Z—C(O)—(CH$_2$)$_o$—R, where Z is O, S or NH, n is 0 to 10, o is 0 to 10 and where R is a hydrogen, a poly(alkylene glycol) molecule or a glycan group; or
- —Y—(CH$_2$)$_n$—Z—C(O)—(CH$_2$)$_o$—R, where Y is an aryl group, O, S or NH, Z is O or NH, n is 0 to 10, o is 0 to 10 and where R is a hydrogen, a poly(alkylene glycol) molecule or a glycan group, or —Y—R, where Y is O or S, R is a hydrogen, a glycan, a poly(alkylene glycol) molecule, aryl or C$_{1-10}$ alkyl;

with the proviso that when R$_2$ is not linked to a poly(alkylene glycol) molecule or a glycan group, it may additionally be selected from hydrogen or an electron withdrawing group, such as halogen (F, Cl, or Br), —NO$_2$, —CO$_2$H, —CO$_2$R$_4$, COR$_4$, —CHO, —CN, —CF$_3$, —SO$_2$NR$_4$R$_5$, alkyl or phenyl, where R$_4$ and R$_5$ are independently selected from hydrogen or C$_{1-10}$ alkyl.

11. A conjugate formed by the reaction of a compound according to claim 10 and one or more thiol groups of a polypeptide.

* * * * *